US010016291B2

(12) United States Patent
Schlun et al.

(10) Patent No.: US 10,016,291 B2
(45) Date of Patent: Jul. 10, 2018

(54) SELF-EXPANSIBLE STENT WITH RADIOPAQUE MARKERS AND METHOD OF MAKING SUCH A STENT (71) Applicant: C. R. Bard, Inc., Murray Hill, NJ (US)

(72) Inventors: Martin Schlun, Herxheim Bei Landau/Pfalz (DE); Pauline Palmer geb Weise, Pforzheim (DE)

(73) Assignee: C. R. Bard, Inc., Murray Hill, NJ (US)

( * ) Notice: Subject to any disclaimer, the term of this patent is extended or adjusted under 35 U.S.C. 154(b) by 728 days.

(21) Appl. No.: 14/270,157

(22) Filed: May 5, 2014

(65) Prior Publication Data
US 2014/0239050 A1    Aug. 28, 2014

Related U.S. Application Data (62) Division of application No. 12/676,584, filed as application No. PCT/EP2008/061775 on Sep. 5, 2008, now Pat. No. 8,721,709.

(30) Foreign Application Priority Data

Sep. 7, 2007    (GB) .................................. 0717481.6

(51) Int. Cl.
*A61F 2/86* (2013.01)
*A61F 2/91* (2013.01)
*A61F 2/915* (2013.01)

(52) U.S. Cl.
CPC .................. *A61F 2/86* (2013.01); *A61F 2/91* (2013.01); *A61F 2/915* (2013.01);
(Continued)

(58) Field of Classification Search
CPC ..................................... A61F 2/86; A61F 2/82
See application file for complete search history.

(56) References Cited

U.S. PATENT DOCUMENTS 5,091,205 A    2/1992  Fan
5,464,419 A   11/1995  Glastra
(Continued)

FOREIGN PATENT DOCUMENTS

DE    04130431 A1    3/1993
DE    29621207 U1    1/1997
(Continued)

OTHER PUBLICATIONS

U.S. Appl. No. 10/362,040, filed Jun. 27, 2003 Office Action dated Aug. 2, 2006.
(Continued)

*Primary Examiner* — Matthew Schall
(74) *Attorney, Agent, or Firm* — Rutan & Tucker, LLP (57) ABSTRACT Pushing a self-expanding stent from one of its ends, during release of the stent at a stenting site in a bodily lumen, by proximal withdrawal of a surrounding sheath, can impose unacceptably high stresses on parts of the strut network of the stent. For location of stents in a bodily lumen, it is customary to equip the end annulus of a stent with radiopaque markers. The present invention involves arranging the markers so that they share with non-marker portions of the end annulus the stresses imposed in the stent by the end pushing, whereby the high stresses are shared more equally by all the struts of the stent in the end annulus.

14 Claims, 3 Drawing Sheets (52) U.S. Cl.
CPC ............... *A61F 2002/91558* (2013.01); *A61F 2230/0013* (2013.01); *A61F 2250/0098* (2013.01); *Y10T 29/49826* (2015.01)

(56) References Cited

U.S. PATENT DOCUMENTS

| | | | |
|---|---|---|---|
| 5,527,353 A | 6/1996 | Schmitt |
| 5,591,223 A | 1/1997 | Lock et al. |
| 5,645,532 A | 7/1997 | Horgan |
| 5,725,572 A | 3/1998 | Lam et al. |
| 5,741,327 A | 4/1998 | Frantzen |
| 5,759,192 A | 6/1998 | Saunders |
| 5,800,511 A | 9/1998 | Mayer |
| 5,824,042 A | 10/1998 | Lombardi et al. |
| 5,824,059 A | 10/1998 | Wijay |
| 5,824,077 A | 10/1998 | Mayer |
| 5,843,118 A | 12/1998 | Sepetka et al. |
| 5,858,556 A | 1/1999 | Eckert et al. |
| 5,861,027 A | 1/1999 | Trapp |
| 5,868,783 A | 2/1999 | Tower |
| 5,922,020 A | 7/1999 | Klein et al. |
| 6,022,374 A | 2/2000 | Imran |
| 6,053,940 A | 4/2000 | Wijay |
| 6,056,187 A | 5/2000 | Acciai et al. |
| 6,086,611 A | 7/2000 | Duffy et al. |
| 6,099,561 A | 8/2000 | Alt |
| 6,174,329 B1 | 1/2001 | Callol et al. |
| 6,241,762 B1 | 6/2001 | Shanley |
| 6,270,524 B1 | 8/2001 | Kim |
| 6,293,966 B1 | 9/2001 | Frantzen |
| 6,312,456 B1 | 11/2001 | Kranz et al. |
| 6,334,871 B1 | 1/2002 | Dor et al. |
| 6,355,057 B1 | 3/2002 | DeMarais et al. |
| 6,379,381 B1 | 4/2002 | Hossainy et al. |
| 6,387,123 B1 | 5/2002 | Jacobs et al. |
| 6,409,752 B1 | 6/2002 | Boatman et al. |
| 6,451,047 B2 | 9/2002 | McCrea et al. |
| 6,471,721 B1 | 10/2002 | Dang |
| 6,475,233 B2 | 11/2002 | Trozera |
| 6,478,816 B1 | 11/2002 | Kveen et al. |
| 6,540,777 B2 | 4/2003 | Stenzel et al. |
| 6,547,818 B1 | 4/2003 | Rourke et al. |
| 6,562,065 B1 | 5/2003 | Shanley |
| 6,585,757 B1 | 7/2003 | Callol |
| 6,605,110 B2 | 8/2003 | Harrison |
| 6,629,994 B2 | 10/2003 | Gomez et al. |
| 6,676,700 B1 | 1/2004 | Jacobs et al. |
| 6,770,089 B1 | 8/2004 | Hong et al. |
| 6,797,217 B2 | 9/2004 | McCrea et al. |
| 6,827,734 B2 | 12/2004 | Fariabi |
| 6,878,162 B2 | 4/2005 | Bales et al. |
| 6,979,346 B1 | 12/2005 | Hossainy et al. |
| 7,060,093 B2 | 6/2006 | Dang et al. |
| 7,135,038 B1 | 11/2006 | Limon |
| 7,175,654 B2 | 2/2007 | Bonsignore et al. |
| 7,462,190 B2 | 12/2008 | Lombardi |
| 7,468,071 B2 | 12/2008 | Edwin et al. |
| 7,479,157 B2 | 1/2009 | Weber et al. |
| 7,691,461 B1 | 4/2010 | Prabhu |
| 7,771,463 B2 | 8/2010 | Ton et al. |
| 7,772,659 B2 | 8/2010 | Rodmacq et al. |
| 8,043,364 B2 | 10/2011 | Lombardi et al. |
| 8,152,842 B2 | 4/2012 | Schlun |
| 8,292,950 B2 | 10/2012 | Dorn et al. |
| 8,322,593 B2 | 12/2012 | Wack |
| 8,403,978 B2 | 3/2013 | Schlun et al. |
| 8,475,520 B2 | 7/2013 | Wack et al. |
| 8,500,793 B2 | 8/2013 | Zipse et al. |
| 8,518,101 B2 | 8/2013 | Dreher |
| 8,551,156 B2 | 10/2013 | Wack et al. |
| 8,574,286 B2 | 11/2013 | Wack |
| 8,721,709 B2 | 5/2014 | Schlun et al. |
| 2002/0007212 A1 | 1/2002 | Brown et al. |
| 2002/0116044 A1 | 8/2002 | Cottone et al. |
| 2002/0116051 A1 | 8/2002 | Cragg |
| 2002/0138136 A1 | 9/2002 | Chandresekaran et al. |
| 2002/0193867 A1 | 12/2002 | Gladdish et al. |
| 2002/0193869 A1 | 12/2002 | Dang |
| 2002/0198589 A1 | 12/2002 | Leong |
| 2003/0055485 A1 | 3/2003 | Lee et al. |
| 2003/0135254 A1 | 7/2003 | Curcio et al. |
| 2003/0144725 A1 | 7/2003 | Lombardi |
| 2003/0216807 A1 | 11/2003 | Jones et al. |
| 2003/0225448 A1 | 12/2003 | Gerberding |
| 2004/0015228 A1* | 1/2004 | Lombardi ................. A61F 2/91 623/1.18 |
| 2004/0015229 A1 | 1/2004 | Fulkerson et al. |
| 2004/0034402 A1 | 2/2004 | Bales et al. |
| 2004/0044401 A1 | 3/2004 | Bales et al. |
| 2004/0073290 A1 | 4/2004 | Chouinard |
| 2004/0073291 A1 | 4/2004 | Brown et al. |
| 2004/0117002 A1 | 6/2004 | Girton et al. |
| 2004/0230293 A1 | 11/2004 | Yip et al. |
| 2004/0236400 A1 | 11/2004 | Edwin et al. |
| 2004/0236409 A1 | 11/2004 | Pelton et al. |
| 2004/0254637 A1 | 12/2004 | Yang et al. |
| 2005/0049682 A1 | 3/2005 | Leanna et al. |
| 2005/0060025 A1 | 3/2005 | Mackiewicz et al. |
| 2005/0149168 A1 | 7/2005 | Gregorich |
| 2005/0172471 A1 | 8/2005 | Vietmeier |
| 2005/0182477 A1 | 8/2005 | White |
| 2005/0222667 A1 | 10/2005 | Hunt |
| 2005/0278019 A1 | 12/2005 | Gregorich |
| 2006/0030934 A1 | 2/2006 | Hogendijk et al. |
| 2006/0064153 A1 | 3/2006 | Langhans et al. |
| 2006/0216431 A1 | 9/2006 | Kerrigan |
| 2006/0241741 A1 | 10/2006 | Lootz |
| 2006/0265049 A1 | 11/2006 | Gray et al. |
| 2007/0112421 A1 | 5/2007 | O'Brien |
| 2007/0219624 A1 | 9/2007 | Brown et al. |
| 2008/0051885 A1 | 2/2008 | Llanos et al. |
| 2008/0188924 A1 | 8/2008 | Prabhu |
| 2009/0125092 A1 | 5/2009 | McCrea et al. |
| 2009/0125099 A1 | 5/2009 | Weber et al. |
| 2009/0200360 A1 | 8/2009 | Wack |
| 2009/0204203 A1 | 8/2009 | Allen et al. |
| 2009/0264982 A1 | 10/2009 | Krause et al. |
| 2010/0016949 A1 | 1/2010 | Wack |
| 2010/0070021 A1 | 3/2010 | Wack et al. |
| 2010/0114298 A1 | 5/2010 | Dorn et al. |
| 2010/0191321 A1 | 7/2010 | Schlun et al. |
| 2010/0204784 A1 | 8/2010 | Molaei et al. |
| 2010/0211161 A1 | 8/2010 | Dreher |
| 2010/0234936 A1 | 9/2010 | Schlun |
| 2010/0249903 A1 | 9/2010 | Wack et al. |
| 2010/0298921 A1 | 11/2010 | Schlun et al. |
| 2011/0196473 A1 | 8/2011 | McCrea et al. |
| 2011/0198327 A1 | 8/2011 | Prabhu |
| 2011/0245905 A1 | 10/2011 | Weber et al. |
| 2011/0319977 A1 | 12/2011 | Pandelidis et al. |
| 2012/0041542 A1 | 2/2012 | Lombardi et al. |
| 2014/0033790 A1 | 2/2014 | Wack et al. |
| 2014/0067045 A1 | 3/2014 | Wack |

FOREIGN PATENT DOCUMENTS

| | | |
|---|---|---|
| DE | 19728337 A1 | 1/1999 |
| DE | 29904817 U1 | 5/1999 |
| DE | 10201151 A1 | 7/2003 |
| DE | 202004014789 U1 | 1/2005 |
| DE | 102004045994 A1 | 3/2006 |
| EP | 0481365 A1 | 4/1992 |
| EP | 0709068 A2 | 5/1996 |
| EP | 0800800 A1 | 10/1997 |
| EP | 0847733 A1 | 6/1998 |
| EP | 0870483 A2 | 10/1998 |
| EP | 1029517 A2 | 8/2000 |
| EP | 1034751 A2 | 9/2000 |
| EP | 1157673 A2 | 11/2001 |
| EP | 1190685 A2 | 3/2002 |
| EP | 1212991 A2 | 6/2002 |
| EP | 1245203 A2 | 10/2002 |
| EP | 1255507 A1 | 11/2002 |
| EP | 1356789 A1 | 10/2003 |

(56) References Cited

FOREIGN PATENT DOCUMENTS

| | | | |
|---|---|---|---|
| EP | 1433438 | A2 | 6/2004 |
| EP | 1488763 | A2 | 12/2004 |
| EP | 1767240 | A1 | 3/2007 |
| EP | 2134301 | A2 | 12/2009 |
| FR | 2626046 | A1 | 7/1989 |
| GB | 453944 | A | 9/1936 |
| JP | 07315147 | A | 12/1995 |
| JP | 2004-506477 | A | 3/2004 |
| JP | 2007-504891 | A | 3/2007 |
| JP | 4827965 | B2 | 11/2011 |
| JP | 4933018 | B2 | 5/2012 |
| WO | 1994017754 | A1 | 8/1994 |
| WO | 1995003010 | A1 | 2/1995 |
| WO | 1996026689 | A1 | 9/1996 |
| WO | 1997033534 | A1 | 9/1997 |
| WO | 1998020810 | A1 | 5/1998 |
| WO | 1999015108 | A2 | 4/1999 |
| WO | 1999038457 | A1 | 8/1999 |
| WO | 1999049928 | A1 | 10/1999 |
| WO | 1999055253 | A1 | 11/1999 |
| WO | 2000045742 | A1 | 8/2000 |
| WO | 2000049971 | A1 | 8/2000 |
| WO | 2000064375 | A1 | 11/2000 |
| WO | 2001001889 | A1 | 1/2001 |
| WO | 2001032102 | A1 | 5/2001 |
| WO | 2001058384 | A1 | 8/2001 |
| WO | 2001076508 | A2 | 10/2001 |
| WO | 2002015820 | A2 | 2/2002 |
| WO | 2002049544 | A1 | 6/2002 |
| WO | 2003055414 | A1 | 7/2003 |
| WO | 2003075797 | | 9/2003 |
| WO | 2003101343 | A1 | 12/2003 |
| WO | 2004019820 | A1 | 3/2004 |
| WO | 2004028408 | A1 | 4/2004 |
| WO | 2004032802 | A2 | 4/2004 |
| WO | 2004058384 | A1 | 7/2004 |
| WO | 2005067816 | A1 | 7/2005 |
| WO | 2005072652 | A1 | 8/2005 |
| WO | 2005104991 | A1 | 11/2005 |
| WO | 2005032403 | A3 | 12/2005 |
| WO | 2006010636 | A1 | 2/2006 |
| WO | 2006010638 | A1 | 2/2006 |
| WO | 2006014768 | A1 | 2/2006 |
| WO | 2006025847 | A2 | 3/2006 |
| WO | 2006036912 | A2 | 4/2006 |
| WO | 2006047977 | A1 | 5/2006 |
| WO | 2006064153 | A1 | 6/2006 |
| WO | 2007073413 | A1 | 6/2007 |
| WO | 2006026778 | A3 | 11/2007 |
| WO | 2007131798 | A1 | 11/2007 |
| WO | 2007135090 | A1 | 11/2007 |
| WO | 2008006830 | A1 | 1/2008 |
| WO | 2008022949 | A1 | 2/2008 |
| WO | 2008022950 | A1 | 2/2008 |
| WO | 2008025762 | A1 | 3/2008 |
| WO | 2008028964 | A2 | 3/2008 |
| WO | 2008055980 | A1 | 5/2008 |
| WO | 2008068279 | A1 | 6/2008 |
| WO | 2008101987 | A1 | 8/2008 |
| WO | 2008119837 | A2 | 10/2008 |
| WO | 2009030748 | A2 | 3/2009 |

OTHER PUBLICATIONS

U.S. 10/362,040, filed Jun. 27, 2003 Office Action dated Dec. 10, 2007.
U.S. Appl. No. 10/362,040, filed Jun. 27, 2003 Office Action dated Feb. 23, 2010.
U.S. Appl. No. 10/362,040, filed Jun. 27, 2003 Office Action dated Jan. 10, 2006.
U.S. Appl. No. 10/362,040, filed Jun. 27, 2003 Office Action dated Jul. 15, 2009.
U.S. Appl. No. 10/362,040, filed Jun. 27, 2003 Office Action dated Jun. 23, 2005.
U.S. Appl. No. 10/362,040, filed Jun. 27, 2003 Office Action dated Jun. 5, 2007.
U.S. Appl. No. 12/300,985, filed Aug. 6, 2010 Final Office Action dated Aug. 15, 2012.
U.S. Appl. No. 12/300,985, filed Aug. 6, 2010 Non-Final Office Action dated Mar. 15, 2012.
U.S. Appl. No. 12/300,985, filed Aug. 6, 2010 Notice of Allowance dated Nov. 16, 2012.
U.S. Appl. No. 12/301,019, filed Feb. 2, 2009 Advisory Action dated Apr. 27, 2011.
U.S. Appl. No. 12/301,019, filed Feb. 2, 2009 Final Office Action dated Feb. 7, 2011.
U.S. Appl. No. 12/301,019, filed Feb. 2, 2009 Non-Final Office Action dated Sep. 3, 2010.
U.S. Appl. No. 12/373,116, filed Jul. 14, 2009 Advisory Action dated Jul. 26, 2011.
U.S. Appl. No. 12/373,116, filed Jul. 14, 2009 Examiner's Answer dated Jan. 3, 2013.
U.S. Appl. No. 12/373,116, filed Jul. 14, 2009 Final Office Action dated Apr. 27, 2011.
U.S. Appl. No. 12/373,116, filed Jul. 14, 2009 Final Office Action dated Mar. 29, 2012.
U.S. Appl. No. 12/373,116, filed Jul. 14, 2009 Non-Final Office Action dated Nov. 10, 2010.
U.S. Appl. No. 12/373,116, filed Jul. 14, 2009 Non-Final Office Action dated Nov. 18, 2011.
U.S. Appl. No. 12/373,116, filed Jul. 14, 2009 Notice of Panel Decision dated Aug. 20, 2012.
U.S. Appl. No. 12/438,102, filed Feb. 19, 2009 Non-Final Office Action dated Nov. 15, 2010.
U.S. Appl. No. 12/438,330, filed Feb. 20, 2009 Advisory Action dated Oct. 14, 2010.
U.S. Appl. No. 12/438,330, filed Feb. 20, 2009 Advisory Action dated Oct. 20, 2011.
U.S. Appl. No. 12/438,330, filed Feb. 20, 2009 Final Office Action dated Aug. 11, 2011.
U.S. Appl. No. 12/438,330, filed Feb. 20, 2009 Non-Final Office Action dated Jun. 7, 2012.
U.S. Appl. No. 12/438,330, filed Feb. 20, 2009 Notice of Allowance dated Sep. 25, 2012.
U.S. Appl. No. 12/438,330, filed Feb. 20, 2009 Office Action dated Aug. 5, 2010.
U.S. Appl. No. 12/438,330, filed Feb. 20, 2009 Office Action dated Mar. 16, 2010.
U.S. Appl. No. 12/438,330, filed Feb. 20, 2009 Office Action dated Mar. 4, 2011.
U.S. Appl. No. 12/438,527, filed Feb. 23, 2009 Advisory Action dated May 24, 2012.
U.S. Appl. No. 12/438,527, filed Feb. 23, 2009 Final Office Action dated Mar. 7, 2012.
U.S. Appl. No. 12/438,527, filed Feb. 23, 2009 Non-Final Office Action dated Jul. 11, 2011.
U.S. Appl. No. 12/440,415, filed Mar. 6, 2009 Final Office Action dated Jan. 10, 2013.
U.S. Appl. No. 12/440,415, filed Mar. 6, 2009 Non-Final Office Action dated Jul. 2, 2012.
U.S. Appl. No. 12/440,415, filed Mar. 6, 2009 Notice of Allowance dated Apr. 3, 2013.
U.S. Appl. No. 12/514,177, filed May 8, 2009 Advisory Action dated Sep. 10, 2012.
U.S. Appl. No. 12/514,177, filed May 8, 2009 Final Office Action dated Apr. 27, 2011.
U.S. Appl. No. 12/514,177, filed May 8, 2009 Final Office Action dated Jul. 11, 2012.
U.S. Appl. No. 12/514,177, filed May 8, 2009 Non-Final Office Action dated Jan. 5, 2011.
U.S. Appl. No. 12/514,177, filed May 8, 2009 Non-Final Office Action dated Mar. 13, 2012.
U.S. Appl. No. 12/517,096, filed Jun. 1, 2009 Final Office Action dated Oct. 31, 2011.
U.S. Appl. No. 12/517,096, filed Jun. 1, 2009 Non-Final Office Action dated Jun. 18, 2012.

(56) References Cited

OTHER PUBLICATIONS

U.S. Appl. No. 12/517,096, filed Jun. 1, 2009 Non-Final Office Action dated May 6, 2011.
U.S. Appl. No. 12/517,096, filed Jun. 1, 2009 Non-Final Office Action dated Nov. 28, 2012.
U.S. Appl. No. 12/517,096, filed Jun. 1, 2009 Notice of Panel Decision dated Mar. 23, 2012.
U.S. Appl. No. 12/528,289, filed Aug. 26, 2009 Non-Final Office Action dated Jan. 27, 2012.
U.S. Appl. No. 12/594,531, filed Oct. 2, 2009 Advisory Action dated Jan. 10, 2012.
U.S. Appl. No. 12/594,531, filed Oct. 2, 2009 Final Office Action dated Nov. 4, 2011.
U.S. Appl. No. 12/594,531, filed Oct. 2, 2009 Non-Final Office Action dated Dec. 17, 2010.
U.S. Appl. No. 12/594,531, filed Oct. 2, 2009 Non-Final Office Action dated May 12, 2011.
Database Wikipedia, Sep. 11, 2007, "Lumen (anatomy)" XP 002453737 abstract.
EP 07787316.4 filed Jul. 10, 2007 Examination Report dated Dec. 23, 2011.
EP 07802603.6 filed Aug. 14, 2007 Office Action dated Dec. 13, 2010.
EP 07820066.4 filed Mar. 31, 2009 Examination Report dated Dec. 27, 2011.
EP 09177588 filed Aug. 14, 2007 Search Report dated Aug. 12, 2011.
EP 12174308.2 filed Apr. 3, 2008 European Search Report dated Sep. 10, 2012.
JP 2010-523512 filed Sep. 5, 2008 Office Action dated Sep. 25, 2012.
PCT/EP2001/009467 International Preliminary Examination Report dated Sep. 17, 2002.
PCT/EP2001/009467 International Search Report dated Feb. 18, 2002.
PCT/EP2007/004407 filed May 16, 2007 International Preliminary Report on Patentability dated Sep. 29, 2008.
PCT/EP2007/004407 filed May 16, 2007 Search Report dated Sep. 26, 2007.
PCT/EP2007/004407 filed May 16, 2007 Written Opinion dated Sep. 26, 2007.
PCT/EP2007/054822 filed on May 18, 2007 International Preliminary Report on Patentability dated Nov. 18, 2008.
PCT/EP2007/054822 filed on May 18, 2007 Search Report dated Sep. 18, 2007.
PCT/EP2007/054822 filed on May 18, 2007 Written Opinion dated Nov. 18, 2008.
PCT/EP2007/057041 filed Jul. 10, 2007 International Preliminary Report on Patentability dated Jan. 13, 2009.
PCT/EP2007/057041 filed Jul. 10, 2007 International Search Report dated Oct. 18, 2007.
PCT/EP2007/057041 filed Jul. 10, 2007 Written Opinion dated Jan. 10, 2009.
PCT/EP2007/058415 filed on Aug. 14, 2007 International Preliminary Report on Patentability dated Feb. 24, 2009.
PCT/EP2007/058415 filed on Aug. 14, 2007 Search Report dated Nov. 30, 2007.
PCT/EP2007/058415 filed on Aug. 14, 2007 Written Opinion dated Nov. 30, 2007.
PCT/EP2007/058416 filed Aug. 14, 2007 International Preliminary Report on Patentability dated Feb. 24, 2009.
PCT/EP2007/058416 filed Aug. 14, 2007 International Search Report dated Nov. 22, 2007.
PCT/EP2007/058416 filed Aug. 14, 2007 Written Opinion dated Feb. 23, 2009.
PCT/EP2007/058912 filed on Aug. 28, 2007 International Preliminary Report on Patentability dated Nov. 5, 2008.
PCT/EP2007/058912 filed on Aug. 28, 2007 Search Report dated Nov. 12, 2007.
PCT/EP2007/058912 filed on Aug. 28, 2007 Written Opinion dated Nov. 12, 2007.
PCT/EP2007/059407 filed Sep. 7, 2007 International Preliminary Report on Patentability and Written Opinion dated Mar. 10, 2009.
PCT/EP2007/059407 filed Sep. 7, 2007 International Search Report dated Jul. 3, 2008.
PCT/EP2007/059407 filed Sep. 7, 2007 Written Opinion dated Mar. 10, 2009.
PCT/EP2007/062155 filed on Nov. 9, 2007 Search Report dated Mar. 12, 2008.
PCT/EP2007/062155 filed on Nov. 9, 2007 Written Opinion dated Mar. 12, 2009.
PCT/EP2007/062155 filed on Nov. 9, 2007 International Preliminary Report on Patentability dated Oct. 15, 2008.
PCT/EP2007/063347 filed Dec. 5, 2007 Search Report dated Jun. 10, 2009.
PCT/EP2007/063347 filed Dec. 5, 2007 Written Opinion dated Jun. 10, 2009.
PCT/EP2007/063347 filed on Dec. 5, 2007 Search Report dated Feb. 4, 2008.
PCT/EP2008/052121 filed Feb. 21, 2008 International Preliminary Report on Patentability dated Aug. 26, 2009.
PCT/EP2008/052121 filed Feb. 21, 2008 International Search Report dated May 19, 2008.
PCT/EP2008/052121 filed Feb. 21, 2008 Written Opinion dated May 9, 2008.
PCT/EP2008/054007 filed Apr. 3, 2008 International Preliminary Report on Patentability dated Jul. 27, 2009.
PCT/EP2008/054007 filed Apr. 3, 2008 Search Report dated Jan. 30, 2009.
PCT/EP2008/054007 filed Apr. 3, 2008 Written Opinion dated Jan. 30, 2009.
PCT/EP2008/061775 filed Sep. 5, 2008 International Search Report dated Apr. 22, 2009.
PCT/EP2008/061775 filed Sep. 5, 2008 Written Opinion dated Apr. 22, 2009.
U.S. Appl. No. 10/362,040, filed Jun. 27, 2003 Advisory Action dated Dec. 16, 2010.
U.S. Appl. No. 10/362,040, filed Jun. 27, 2003 Advisory Action dated Jan. 9, 2009.
U.S. Appl. No. 10/362,040, filed Jun. 27, 2003 Advisory Action dated Nov. 29, 2006.
U.S. Appl. No. 10/362,040, filed Jun. 27, 2003 Final Office Action dated Aug. 30, 2010.
U.S. Appl. No. 10/362,040, filed Jun. 27, 2003 Notice of Allowance dated Jun. 22, 2011.
U.S. Appl. No. 10/362,040, filed Jun. 27, 2003 Office Action dated Aug. 18, 2008.
U.S. Appl. No. 12/594,531, filed Oct. 2, 2009 Non-Final Office Action dated Oct. 2, 2012.
U.S. Appl. No. 12/676,584, filed Mar. 4, 2010 Non-Final Office Action dated May 24, 2013.
U.S. Appl. No. 12/676,584, filed Mar. 4, 2010 Notice of Allowance dated Dec. 27, 2013.
U.S. Appl. No. 13/279,189, filed Oct. 21, 2011 Examiner's Answer dated Feb. 14, 2014.
U.S. Appl. No. 13/279,189, filed Oct. 21, 2011 Final Office Action dated May 2, 2013.
U.S. Appl. No. 13/279,189, filed Oct. 21, 2011 Non-Final Office Action dated Oct. 17, 2012.

\* cited by examiner

SELF-EXPANSIBLE STENT WITH RADIOPAQUE MARKERS AND METHOD OF MAKING SUCH A STENT

PRIORITY

This application is a division of U.S. patent application Ser. No. 12/676,584, now U.S. Pat. No. 8,721,709, which was filed as a U.S. national stage application under 35 USC § 371 of International Application No. PCT/EP2008/061775, filed Sep. 5, 2008, which claims priority to United Kingdom Patent Application No. 0717481.6, filed Sep. 7, 2007, each of which is incorporated by reference in its entirety into this application.

FIELD OF THE INVENTION

This invention relates to a radially self-expansible stent with a plurality of radiopaque markers attached to at least one of its ends, and to a method of making such a stent.

BACKGROUND ART

Vascular stents are commonly used for the treatment of various vessel diseases. They are implanted transluminally using a catheter delivery system, to advance them to a stenting site, where they expand in order to widen the clogged or narrowed blood vessel. During the implantation procedure, the exact position of the stent within the vessel is monitored, mainly using X-ray imaging techniques. In order to ensure accurate placement, a good visibility of the stent is crucial. In general, this is achieved by attaching suitable markers which are made from materials with a radiopacity larger than that of the stent material. In addition, these markers have to be sufficiently large to provide a good X-ray contrast. For a precise determination of the stent position during delivery, it is advantageous to place the markers at both ends of the stent.

A tubular stent with a plurality of radiopaque markers attached to selected inflection zones around its circumference is disclosed in WO 2002/015820. The markers are spoon-shaped in a way that almost a complete ring of marker material is formed in the radially compressed state of the stent, providing a particularly high level of radiopacity during transluminal delivery. Thereby, an increase in visibility to radiation is achieved without any increase in the wall thickness of the stent at the position of the markers, maintaining a large radial opening for fluid flow as well as a small cross-sectional profile. Ideally, the number of markers in such a ring of markers as described above is to be kept small, so that each marker is large enough to facilitate sufficient visibility even in the radially expanded state of the stent. Furthermore, the number of marker/inflection zone joints should be kept at a minimum in order to reduce the risk of loss of a marker in the body following failure of such a joint after the stent has been placed.

For the case of self-expansible stents, delivery to the narrowed portion of the blood vessel is performed with the use of a co-axial catheter delivery system. Hereby, the stent is kept in its radially compressed state by an outer sheath. A co-axial cylinder inside the sheath is used for displacing the stent axially, relative to the outer sheath. Once the stent has been placed at the desired position within the vessel, the outer sheath is withdrawn while the inner cylinder pushes against one end of the compressed stent, precipitating the release of the stent from the delivery system. This procedure can impose on a stent such as the one disclosed in WO 2002/015820 stresses concentrated on the radiopaque markers which protrude axially beyond the axial end of the matrix of struts of the stent annulus. This stress, concentrating at the joints between the markers and the inflection zones from which they are cantilevered, has been identified by the present inventor as a feature that can and should be reduced or even eliminated.

This patent application declares the priority of GB 0 717 481.6. In that GB priority application the search report conducted on the claims by the UK Patent Office cited the following documents: WO 2006/047977; DE 20 2004 014 789; WO 2004/028408 and EP 1 433 438. The disclosures of the first two citations are of the same invention from the same inventor.

WO 2006/047977 discloses a stent with an end annulus that carries radiopaque marker material in recesses in receiving elements of the stent metal. Thus, the marker material has exposed luminal and abluminal part-cylindrical opposed major surfaces and a thickness corresponding to that of the receiving element that surrounds the entire peripheral edge of the marker between its major surfaces. The marker has a width in the circumferential direction of the stent annulus, that is smaller than the circumferential length of the portion of the stent in which the marker is received. The marker enters the recess from a position radially outside the stent annulus, conical surface portions of the marker and the receiving portion serving to guide the marker into a snugly fitting disposition within the receiving portion, supported in all sides by the receiving portion.

The disclosure of WO 2004/028408 is similar. As to EP 1 433 438, it discloses other sorts of radiopaque markers on stents, notably a wire of radiopaque material wound around a strut of the stent, or a sleeve of radiopaque material crimped around a strut of the stent. Self-evidently, the stent is locally thicker in the radial direction, where such markers are located.

SUMMARY OF THE INVENTION

The main objective of the present invention is to provide a self-expansible stent with radiopaque markers attached to it that offers a high degree of mechanical stability during release of the stent from the delivery system while maintaining a good visibility upon exposure to radiation. This aim is achieved by a self-expansible stent with the technical features of claim 1. Preferred embodiments of the invention follow from the subclaims.

The present invention provides a radially self-expansible stent with two end annuli for delivery by a co-axial catheter delivery system. The end annulus to be pushed during release of the stent has a plurality of spaced inflection zones distributed in its circumference, some of which carry a radiopaque marker. The idea is to get all the inflection zones to share the release stresses, not just the ones that carry a radiopaque marker. In general, the term "inflection zone" as used herein refers to a region where two or more strut ends are connected or where two or more struts intersect. It is, however, not restricted to this interpretation. A large number of different strut patterns are being used, or have at least been proposed, for tubular stents. Each of these patterns will have points which define an end to the stent tube and which allow for the attachment of a marker. Our definition of the term "inflection zone" is such that these end points are included.

The radiopaque markers are shaped and located on the selected inflection zones such that the compressive stress exerted on the end annulus during release of the stent is shared between the markers and the inflection zones that do not carry a marker. In this way, the strain on the marker/inflection zone joints is minimised, reducing the risk of physical damage, such as breakage or deformation. This concept is applicable to any stent design and allows for the use of only a small number of markers while the stability of the stent is secured. Keeping the number of markers at a minimum has significant advantages. First, having fewer marker/inflection zone joints reduces the danger of severed or bent markers. Self-expansible stents are extremely elastic but nevertheless not invulnerable to distortion. Fatigue performance is of vital importance with vascular stents, which flex with every heartbeat. Any stress that a stent matrix suffers locally, that exceeds the maximum planned for in the Government regulatory fatigue-testing protocol can adversely affect the fatigue life of the stent. This fact emphasizes the importance of a robust stent design, since even the slightest damage to the joints occurring during the release of the stent may shorten the service life of the stent. Furthermore, the circumference of the ring formed by the ensemble of markers in the radially compressed state of the stent is limited by the circumference of the stent tube itself. Thus, keeping the number of markers small allows for larger marker sizes and consequently an improved visibility of the stent in the radially expanded state.

So-called "ring stents" exhibit a plurality of rings arranged along their axial length which are interconnected between ring ends and have a plurality of inflection zones distributed in the circumference of the ring ends. In one embodiment, each of these ring ends comprises more inflection zones than the end annulus of the stent. Since, in the radially compressed state, the stent has a homogeneous circumference throughout its structure, the circumference of the end annulus of the stent will be the same as that of the ring ends, despite comprising less inflection zones. Therefore, the circumferential extent of the inflection zones that carry a marker can be increased, allowing for the attachment of larger markers, which is advantageous for reasons of visibility as discussed above. Even more space for the markers can be created within the end annulus of the stent if the inflection zones of the end annulus of the stent that do not carry a marker have a smaller circumferential extent than the inflection zones distributed in the circumference of the ring ends. Therefore, the above arrangement facilitates a possible increase in marker size without changing the number of inflection zones of the stent rings which may affect the mechanical properties of the stent, such as stability and elasticity.

A further way of creating more space for the markers within the end annulus of the stent is given in another preferred embodiment, where the inflection zones of the end annulus of the stent that do not carry a marker have a larger axial length parallel to the long axis of the stent than the inflection zones distributed in the circumference of the ring ends.

Preferably, the markers are bonded to the inflection zones at a glue interface, more preferably, by a weld. The form of the weld is hereby determined by the shape and the size of the marker.

In a preferred embodiment, the inflection zones that carry a marker differ in shape, size or both shape and size from the inflection zones that do not carry a marker. The inflection zones that carry a marker may, for example, have a smaller size so as to leave more space for the attached markers or a shape particularly suited for a certain type of weld (depending on the shape and size of the marker). In one embodiment, each inflection zone is present as a stem with an axial length parallel to the long axis of the stent. Preferably, the inflection zone stems that carry a marker have a smaller length than the inflection zone stems that do not carry a marker. This arrangement allows for the accommodation of portions of the markers (or even whole markers) between the neighbouring longer inflection zones.

Preferably, the markers and the inflection zones have the same thickness but markers with a greater radial thickness are not excluded. On the one hand, an increase in marker thickness beyond the stent annulus wall thickness is not desirable, since a large radial opening for fluid flow as well as a small cross-sectional profile of the stent ought to be maintained. On the other hand, both the radiopacity and the mechanical properties of the markers depend on their thickness. Consequently, too thin a marker will give a poor contrast when exposed to radiation and may be prone to deformation or even breakage.

In a preferred embodiment, each marker subtends a larger arc of the circumference of the end annulus than each inflection zone that does not carry a marker, improving the visibility of the stent ends. In any event, the width of the marker, in the circumferential direction, will generally be as larges as, or larger than, but not smaller than, the circumferential width of the inflection zone to which the marker is attached.

A number of different materials may be used for the fabrication of the stent and the radiopaque markers. Preferably, the stent is made from a nickel titanium shape memory alloy. Such an alloy provides the mechanical properties necessary for reliable stent operation, namely a high degree of elasticity and physical stability. The radiopaque markers are preferably made from tantalum, gold, or a ternary alloy made from nickel, titanium and a third, radiopaque metal. All these metals offer a high level of radiopacity. Both the above stent and marker materials are non-toxic and provide a good biological compatibility with the human body. For nickel titanium stents, markers of tantalum are of special interest because their electrochemical potentials are so similar.

In another preferred embodiment, the markers do not extend axially beyond the inflection zones which do not carry a marker, in the radially compressed state of the stent. This arrangement can be accomplished, for example, by making the inflection zones that carry a marker shorter than the ones that do not carry a marker. Preferably, during release of the stent from the delivery system, both the markers and the inflection zones which do not carry a marker abut, or are otherwise in physical contact with, the pushing part of the delivery system, i.e., the co-axial inner cylinder. In such a configuration, the compressive stress exerted on the end annulus during release of the stent is shared between the markers and the inflection zones without markers, minimising the risk of physical damage to the stent. A marker size large enough for excellent visibility can still be maintained by choosing a small number of inflection zones in the end annulus of the stent and by making the inflection zones that carry a marker sufficiently short.

In another preferred embodiment, portions of the periphery of the markers rest on the neighbouring inflection zones in the radially compressed state of the stent, such that the compressive stress exerted by the delivery system on the markers during release of the stent is delivered to the neighbouring inflection zones by the markers. Preferably, in this configuration the markers stand axially proud of the inflection zones that do not carry a marker. In this configuration, an increase in marker size can be achieved, while the distribution of the applied pressure between markers and inflection zones without markers is still maintained.

The markers can be welded to the inflection zones by methods described in above-mentioned WO 2002/015820. In a variation, however, the markers and inflection zones can be advanced towards each other along the longitudinal axis of the stent without any relative radial movement, for example by providing a form fit between the respective marker and inflection zone faces that face each other across the welding zone. The form fit can be accomplished by co-operating ramp surfaces on the marker and the inflection zone, that work together to inhibit any relative circumferential sliding movement in the width direction of the marker and inflection zone. In this way, the markers are guided into a position circumferentially aligned with the respective inflection zone, prior to being welded to that inflection zone.

DETAILED DESCRIPTION OF PREFERRED EMBODIMENTS

Figure 1:
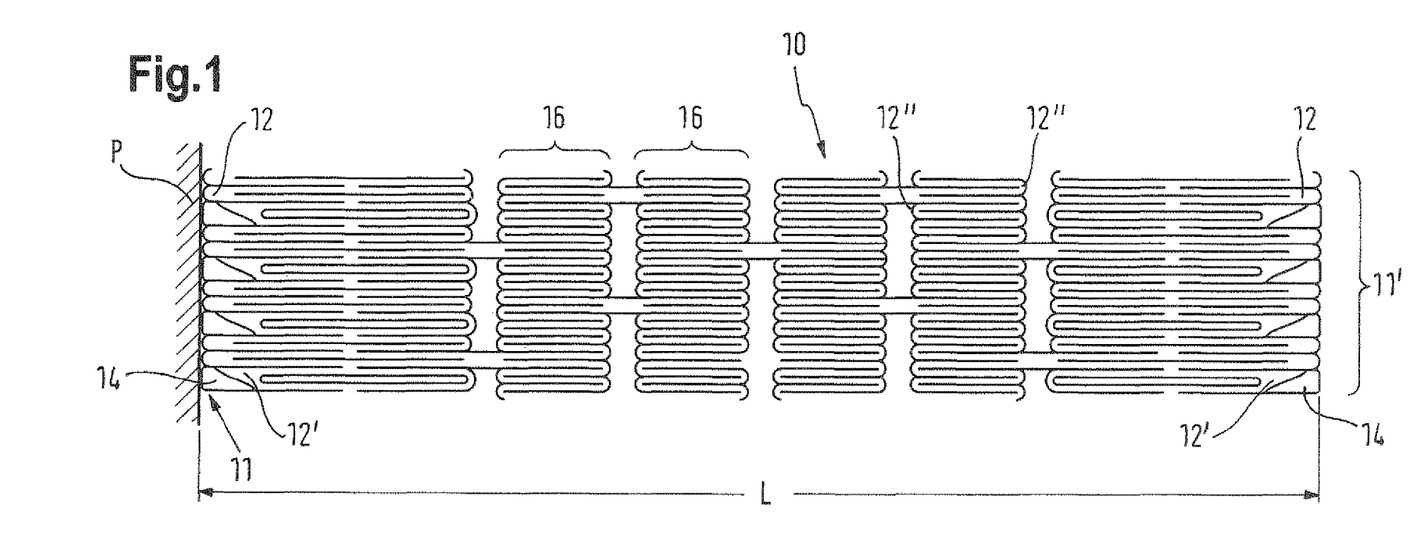
FIG. 1 shows a laser cutting of a stent with radiopaque markers attached to it, according to a first preferred embodiment.

FIG. 1 shows a laser cutting of a radially self-expansible stent 10 made from Nitinol with radiopaque markers 14 made from Tantalum attached, according to a first preferred embodiment. The markers 14 are welded to the inflection zones 12' and extend as far as the inflection zones that do not carry a marker 12. In this way, the compressive stress exerted on the end annulus 11 by a stent pusher annulus P during release of the stent is shared between the markers 14 and the inflection zones 12 that do not carry a marker because what abuts the pusher P is not just the markers 14 but also the inflection zones 12 that carry no marker 14. The stent comprises four interconnected rings 16 with fourteen inflection zones 12" in the circumference of each ring end. In contrast to this, the end annuli 11, 11' only have twelve inflection zones 12, 12'. This allows for a larger circumferential extent of the inflection zones 12' and the markers 14 attached thereto since the circumferential extent of the inflection zones 12 is identical to that of the inflection zones 12". In addition to this, the axial length of inflection zones 12 is larger than that of inflection zones 12", allowing for longer markers. Thus, the present embodiment is specifically designed for accommodating large markers 14 in order to optimise the visibility of the stent 10.

Figure 2:
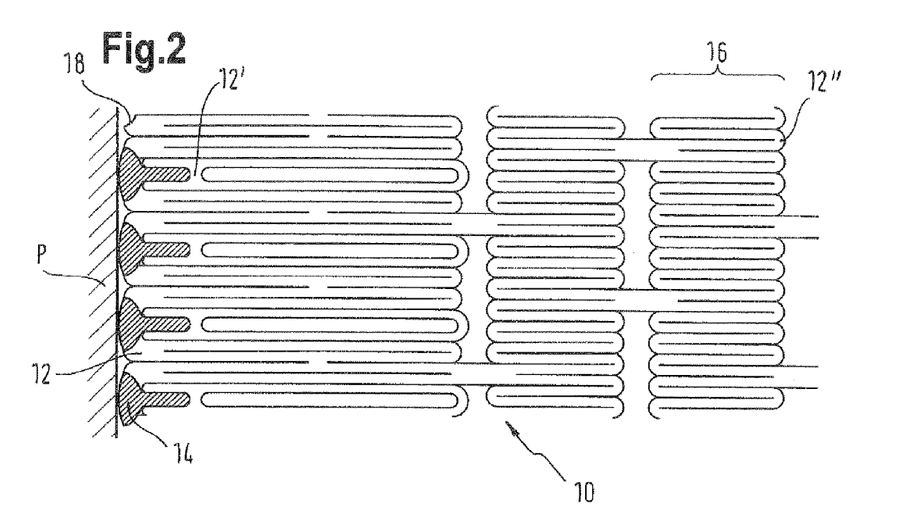
FIG. 2 shows one end of a laser cutting of a stent with radiopaque markers attached to it, according to a second preferred embodiment.
Figure 3:
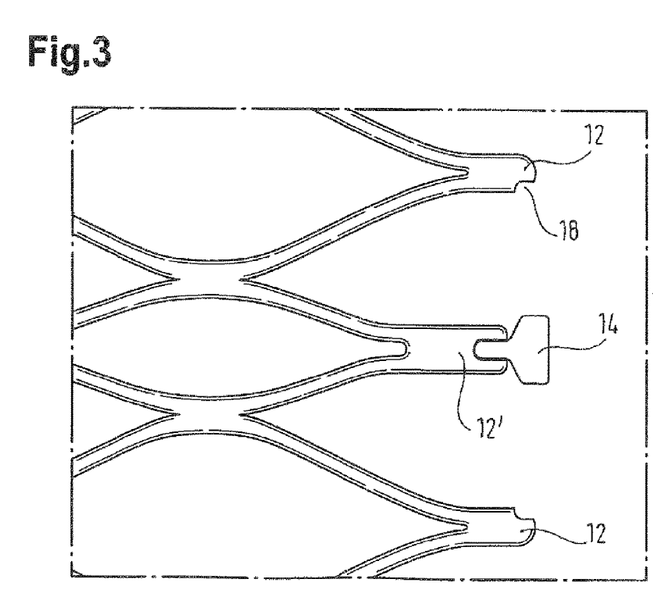
FIG. 3 shows a portion of the end annulus in the radially expanded state of the stent, according to a second preferred embodiment.

FIG. 2 shows one end of a laser cutting of a stent 10 made from Nitinol with radiopaque markers 14 made from Tantalum attached to it, according to a second preferred embodiment. The markers 14 are welded to the inflection zones 12' and stand axially proud of the inflection zones 12 that do not carry a marker 14. As can be seen, the shape of inflection zones 12' is adapted in order to allow for a robust welded connection with marker 14 and differs significantly from that of inflection zones 12. The increased circumferential extent of inflection zones 12' as compared to inflection zones 12 is facilitated by the difference in the number of inflection zones 12, 12', 12" between the ends of rings 16 and the end annulus 11, analogous to the first preferred embodiment. Furthermore, inflection zones 12 have grooves 18 at their top ends which are shaped to accommodate the peripheral portions of the T-shaped markers 14 in the radially compressed state of the stent 10. In this way, despite the fact that during the release of the stent 10 only the markers 14 are in physical contact with the pushing part P of the delivery system, the compressive stress exerted on the markers is shared between the markers and the neighbouring inflection zones. The present configuration allows for the accommodation of particularly large markers 14 while at the same time maintaining the stability of the stent 10. FIG. 3 shows a portion of the end annulus 11 in the radially expanded state of the stent 10, according to the present embodiment. Here, the grooves 18 are more clearly visible.

Figure 4:
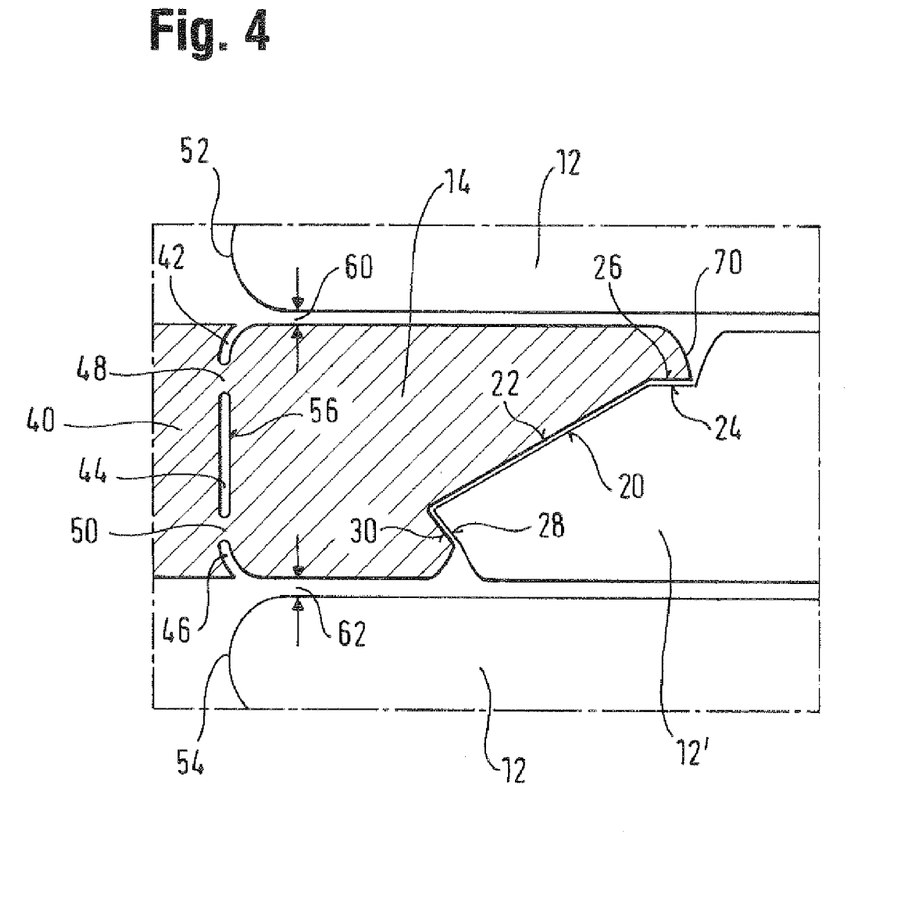
FIG. 4 is a view of a fragment of one end of a stent, that shows an inflection zone comprising a marker and flanked by longer inflection zones that do not carry any marker.

Turning to FIG. 4, here we see a tantalum marker 14 located between two long inflection zones 12 and to be welded to a short inflection zone 12'. The marker is joined by two small bridges 48, 50 to a tantalum tube 40. These bridges 48, 50 facilitate separation of the marker 14 from the tantalum tube 40 in an uncomplicated manner by the application of an external force, once the welding has been performed. However, the bridges 48, 50 are not a required feature and other methods may be applied for separating the marker 14 from the tantalum tube 40. In particular, a single laser may be used for both welding the marker 14 to the inflection zone 12' and separating the marker 14 from the tantalum tube 40. In this case, first the welding step is performed and subsequently the separation step is carried out after increasing the output power of the laser. Both these steps can be carried out in a single operation, thus improving the efficiency of the fabrication process. If the above described separation method is used, the connection profile between tantalum tube 40 and marker 14 may be of any conceivable form, for example, a single wider bridge. As explained in WO 2002/015820 mentioned above, the tantalum tube 40 and the tube of nickel titanium shape memory alloy of the stent and the inflection zones 12 are approximated axially, whereupon the facing surfaces 20 and 22 of the inflection zone 12 and marker 14 come into facing relationship, ready for welding together. The skilled reader will appreciate that during this approximation by axial approach there is no need for any relative radial movements between the two work pieces.

As to circumferential alignment between the marker 14 and the inflection zone 12, we see in FIG. 4 how the facing surfaces 20, 22 incorporate form fit portions 24, 26, 28, 30 that work together to guide the advancing marker 14 into alignment with the inflection zone so there is clearance 60, 62 between the marker 14 and the two flanking inflection zones 12, respectively.

The facing surfaces 20, 22 achieve a circumferential guiding function through a mechanical "form fit". As the nose 70 of the marker 14 approaches the inflection zone 12' it can slide along the facing surface 20 until it goes past the axially aligned straight edge 24 when straight edge 26 of the nose 70 will then be facing the straight edge 24.

By then, however, the V-shaped recess in the facing surface 22 of the marker, flanked by reverse-angled surface 30, will have received the V-shaped peak in the facing surface 20 of the inflection zone 12' flanked by reverse-angled surface portion 28 in the facing surface 20. Any widening in the gap between surfaces 24 and 26 is prevented by the abutment of surfaces 28 and 30 (and vice versa). In this way, the marker 14, approximated to the inflection zone 12' and ready for welding to it, has no freedom any more to move circumferentially relative to the inflection zone 12'. Exactly in this "welding ready" disposition, the end surface 56 of the marker 14 lies in the same plane, transverse to the axis of the stent, as the end surfaces 52 and 54 of the flanking inflection zones 12. Thus, when the stent is pushed by a pusher P, the pushing force is imposed equally on all of end surfaces 52, 54 and 56.

The illustrated embodiments are by way of example and the skilled reader will appreciate that features can be isolated from one embodiment and can be taken and used in other embodiments within the scope of the claims which follow.

What is claimed is:

1. A method of fastening a radiopaque marker to an A-vertex of a radially self-expanding stent, in which the marker is advanced into a fastening position and then welded to the A-vertex creating a welding zone between the A-vertex and the marker, wherein:
    the relative movement between the marker and the A-vertex lacks a component orthogonal to the stent's longitudinal axis, and
    an end surface of the marker and end surfaces of B-vertexes that circumferentially flank the marker and the A-vertex all lie in a plane orthogonal to the longitudinal axis.

2. The method of claim 1, wherein the marker and the A-vertex fit to inhibit circumferential sliding movement.

3. The method of claim 2, wherein ramp surfaces on the marker and the A-vertex cooperate to circumferentially align the marker and the A-vertex.

4. The method of claim 3, wherein the end surface of the marker and the end surfaces of the B-vertexes define an end of a stent and markers object.

5. The method of claim 4, wherein the B-vertexes comprise two, intersected strut ends, the strut ends being circumferentially offset from the marker such that lateral surface of the marker faces a lateral surface of at least one of the strut ends.

6. The method of claim 5, wherein the A-vertex has a shape different from the B-vertexes.

7. The method of claim 6, wherein the B-vertexes comprise a portion shaped to correspond to a portion of the marker.

8. The method of claim 7, wherein the A-vertex has a size different from the B-vertexes.

9. A method comprising:
    providing a radiopaque marker;
    providing a self-expanding stent comprising an A-vertex positioned between two circumferentially arranged, B-vertexes;
    and
    advancing the marker into a fastening position abutting the A-vertex, until a marker end and ends of the two B-vertexes all lie in a plane orthogonal to a longitudinal axis of the stent,
wherein advancing is with longitudinal movement and without radial movement.

10. The method of claim 9, wherein at least one of the B-vertexes comprises two, intersecting strut ends that abut the marker, are circumferentially offset from the marker, and have a contour matching the marker's abutting contour.

11. The method of claim 10, wherein the A-vertex has a shape different from the B-vertexes.

12. The method of claim 11, wherein at least one of the B-vertexes comprises a portion shaped to correspond to a portion of the marker.

13. The method of claim 12, wherein the A-vertex has a size different from the B-vertexes.

14. The method of claim 13, wherein the marker further comprises a tongue that engages an elongated opening in the A-vertex.

* * * * *